United States Patent
Conger

(10) Patent No.: US 8,588,939 B2
(45) Date of Patent: *Nov. 19, 2013

(54) METHOD OF ASSEMBLING AN IMPLANTABLE MEDICAL LEAD HAVING PASSIVE LOCK MECHANICAL BODY TERMINATIONS

(71) Applicant: Pacesetter, Inc., Sylmar, CA (US)

(72) Inventor: Steven R. Conger, Agua Dulce, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/647,886

(22) Filed: Oct. 9, 2012

(65) Prior Publication Data

US 2013/0025122 A1 Jan. 31, 2013

Related U.S. Application Data

(62) Division of application No. 12/501,950, filed on Jul. 13, 2009, now Pat. No. 8,321,033.

(51) Int. Cl.
*A61N 1/05* (2006.01)

(52) U.S. Cl.
USPC ........... 607/116; 607/117; 607/118; 607/119; 607/120; 607/121; 607/122

(58) Field of Classification Search
USPC ............................ 607/116–122; 600/373–381
See application file for complete search history.

(56) References Cited

U.S. PATENT DOCUMENTS

| | | | |
|---|---|---|---|
| 5,246,014 A | | 9/1993 | Williams et al. |
| 5,344,439 A | | 9/1994 | Otten |
| 5,439,485 A | * | 8/1995 | Mar et al. ...................... 607/119 |
| 5,522,872 A | | 6/1996 | Hoff |
| 6,970,747 B2 | | 11/2005 | Kokones et al. |
| 7,146,222 B2 | | 12/2006 | Boling |
| 7,630,749 B2 | | 12/2009 | Squeri |
| 8,321,033 B2 | * | 11/2012 | Conger ........................ 607/116 |
| 2003/0199951 A1 | | 10/2003 | Pardo et al. |

FOREIGN PATENT DOCUMENTS

| | | |
|---|---|---|
| EP | 1935449 A1 | 6/2008 |
| WO | 2005011806 A1 | 2/2005 |
| WO | 2005011807 A1 | 2/2005 |
| WO | 2008054259 A1 | 5/2008 |

OTHER PUBLICATIONS

NonFinal Office Action, mailed Mar. 29, 2012—U.S. Appl. No. 12/501,950.
Final Office Action, mailed Jul. 25, 2012—U.S. Appl. No. 12/501,950.
Notice of Allowance, mailed Oct. 2, 2012—U.S. Appl. No. 12/501,950.

* cited by examiner

*Primary Examiner* — Carl H Layno
*Assistant Examiner* — Jon Eric C Morales

(57) ABSTRACT

Disclosed herein is a method of assembling an implantable medical lead configured to receive a stylet. The lead is provided with a tubular insulation layer, an electrode is disposed on the tubular insulation layer, an electrical conductor is routed through the tubular insulation layer, and a stylet stop is inserted into a distal end of the tubular insulation layer. The electrical conductor is directly and mechanically connected to the stylet stop and is in electrical communication with the electrode.

9 Claims, 12 Drawing Sheets

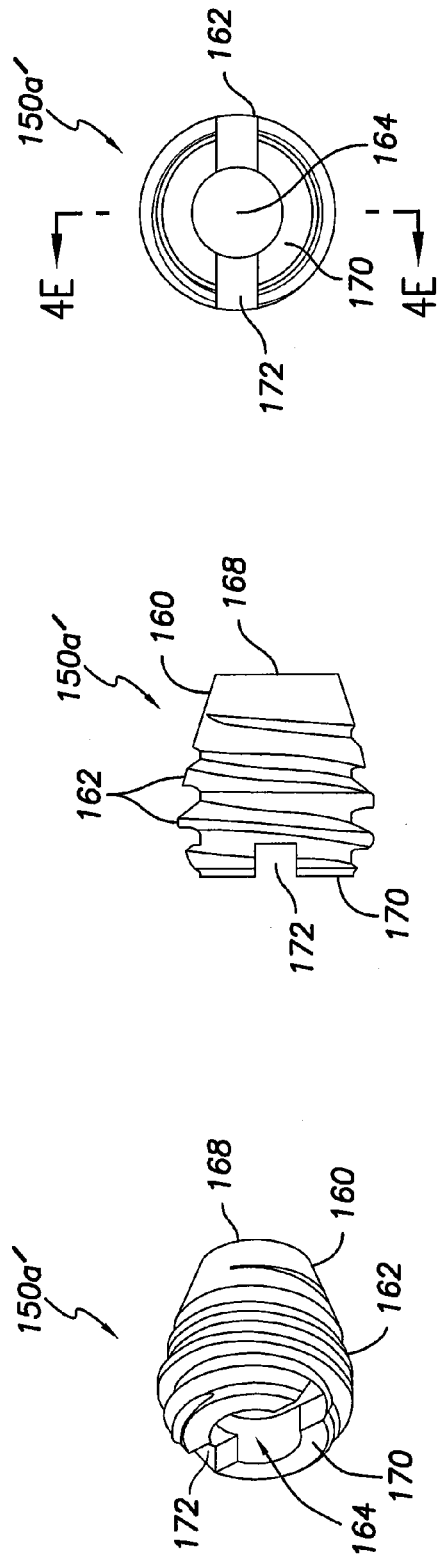
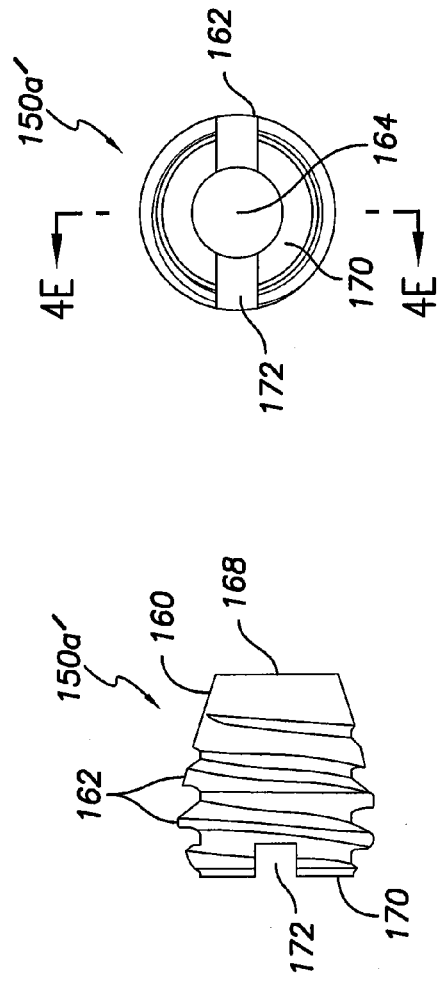
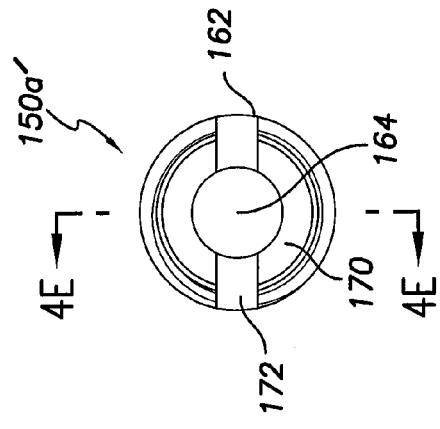
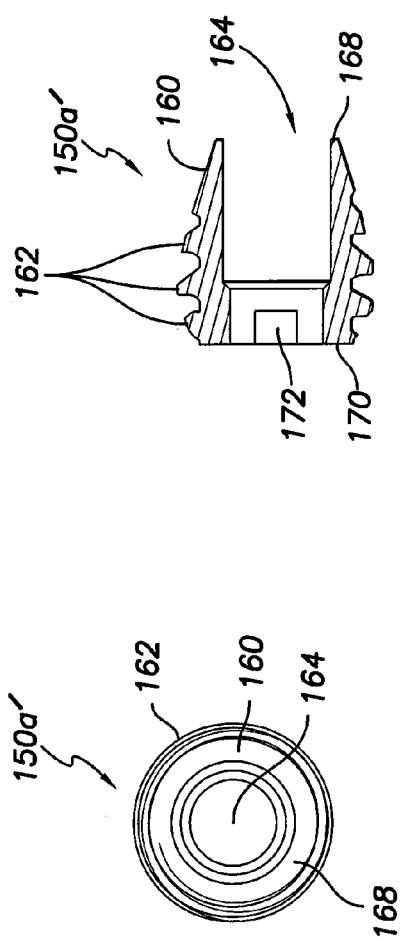
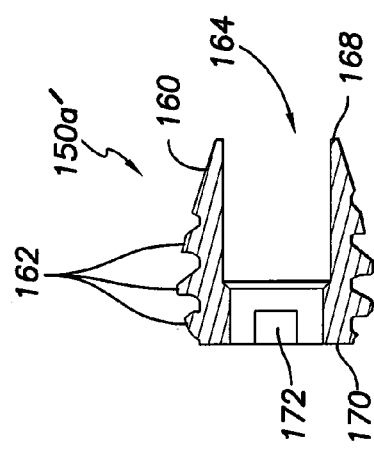

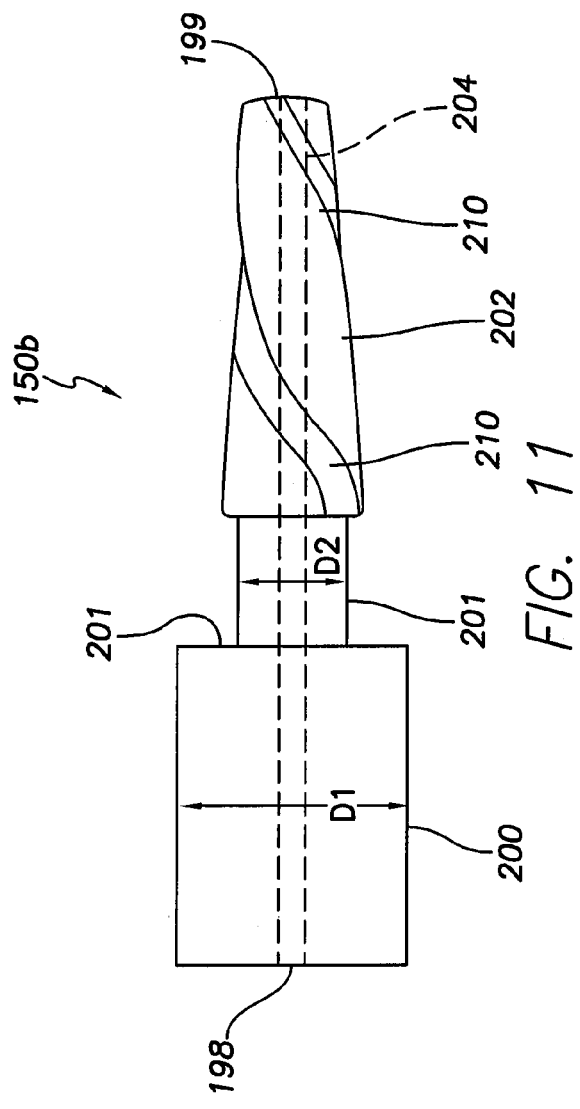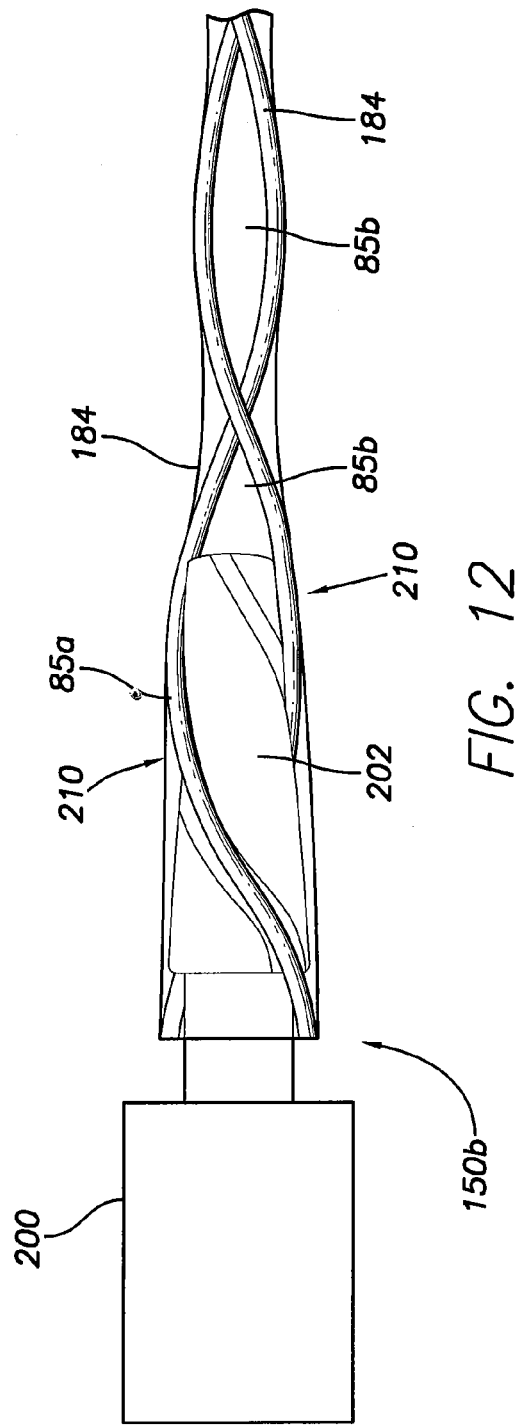

METHOD OF ASSEMBLING AN IMPLANTABLE MEDICAL LEAD HAVING PASSIVE LOCK MECHANICAL BODY TERMINATIONS

CROSS REFERENCE TO RELATED APPLICATIONS

This application is a division of U.S. patent application Ser. No. 12/501,950, filed Jul. 13, 2009, now U.S. Patent No. 8,321,033.

FIELD OF THE INVENTION

The present invention relates to medical apparatus and methods. More specifically, the present invention relates to implantable medical leads and methods of manufacturing such leads.

BACKGROUND OF THE INVENTION

Implantable pulse generators 15, such as pacemakers, defibrillators, implantable cardioverter defibrillators ("ICD") and neurostimulators, provide electrotherapy via implantable medical leads 10 to nerves, such as those nerves found in cardiac tissue, the spinal column, the brain, etc. Electrotherapy is provided in the form of electrical signals, which are generated in the pulse generator 15 and travel via the lead's conductors to the electrotherapy treatment site.

Lead conductors 85 are typically in the form of flexible single wires or multi-filar cables. These lead conductors 85 may be individually electrically insulated with their own dedicated insulation jackets or may be without a dedicated insulation jacket, instead having to rely on the concentric insulation layers of the lead body.

New lead technologies and treatment programs make it desirable to place electronic lead components along the length of the lead body 50 of a lead 10. For example, as indicated in FIG. 1, which is an isometric view of a proposed lead body 50 that may be coupled to a pulse generator 15 via a lead connector end 35 having a pin contact 55 and ring contacts 61-62, multiple fragile electronic chips electrodes 80-83 may be located along the lengths of the conductors 85$a$, 85$b$, 85$c$ extending between the proximal and distal ends 40, 45 of the lead body 50. The placement of such electronic chip electrodes 80-83 necessitates multiple closely spaced couplings of the straight-routed conductors 85$a$-85$c$ with the terminals of the electronic chip electrodes 80-83. Such close spaced couplings with conductors 85$a$-85$c$ substantially reduce the ability of the conductors 85$a$-85$c$ to displace and conform to displacement of the lead body 50, potentially resulting in rapid failure of the conductors 85$a$-85$c$. Also, the conductors 85$a$-85$c$ result in substantial strain in the couplings, causing rapid failure of the couplings as well.

There is a need in the art for a lead having a conductor configuration that provides improved resistance to strain induced conductor failure, reduced lead body stiffness and reduced manufacturing costs. There is also a need in the art for a method of manufacturing a lead having such a conductor configuration.

BRIEF SUMMARY OF THE INVENTION

Disclosed herein is an implantable medical lead configured to receive a stylet. In one embodiment, the lead includes a tubular body, a stylet stop, a most distal electrode, a lead connector end, and a conductor. The body includes a distal end, a proximal end, and a lumen longitudinally extending through the tubular body between the proximal end and distal end and configured to receive the stylet. The stylet stop is coupled to the body near the distal end. The most distal electrode is coupled to the body proximal the stylet stop. The lead connector end is coupled to the body near the proximal end and includes at least one electrical contact. The conductor proximally begins at the lead connector end and extends through the body and mechanically connects to the stylet stop. The conductor places the electrical contact in electrical communication with the most distal electrode.

Also disclosed herein is an implantable medical lead configured to receive a stylet. In one embodiment, the lead includes a tubular body and a structure. The tubular body includes a distal end and a proximal end. The body is configured to receive the stylet. The structure longitudinally extends through a wall of the body between the distal end and the proximal end. The structure is anchored within the body such that a tensile force arising within the body by the stylet being extended through the body causes the tensile force to be substantially carried by the structure.

Another implantable medical lead is disclosed herein. In one embodiment, the lead includes a longitudinally extending body, a stylet stop, an electrode, and an electrical conductor. The stylet stop is in the body. The electrode is mounted on the lead body. The electrical conductor extends through a wall of the body, is directly mechanically connected to the stylet stop, and is in electrical communication with the electrode. In one embodiment, the lead further includes a grooved member including a groove defined in an outer surface of the member, wherein the conductor is received in the groove and the member is near a proximal end of the body.

Also disclosed herein is a method of assembling an implantable medical lead, the method comprising: providing a tubular insulation layer; routing an electrical conductor through the insulation layer; and inserting a stylet stop into a distal end of the insulation layer such that the conductor is positioned between the insulation layer and the stylet stop. In one embodiment, the method further includes providing a grooved member in a proximal end of the insulation layer and routing the conductor along a groove extending along the member.

While multiple embodiments are disclosed, still other embodiments of the present invention will become apparent to those skilled in the art from the following Detailed Description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIGS. 4A-4E are, respectively, distal isometric, side, distal end, proximal end, and longitudinal cross sectional views of a stylet stop shell of the stylet stop.

FIG. 11 is a longitudinal side view of a second embodiment of the proximal termination member.

FIG. 12 is the same view as FIG. 11, except with the conductors are extending along the proximal portion.

DETAILED DESCRIPTION

Figure 1:
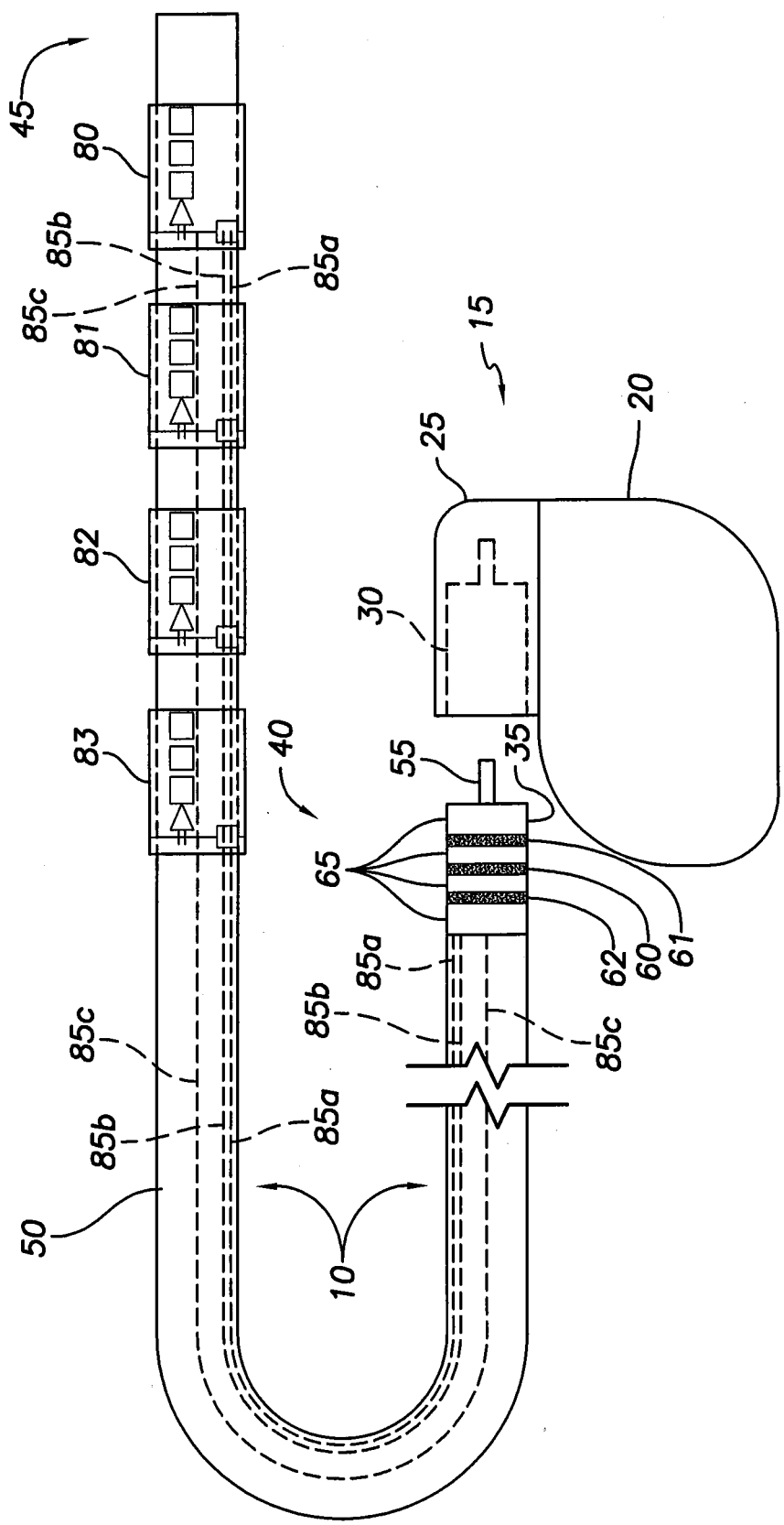
FIG. 1 is an isometric view of a proposed lead body, wherein multiple fragile electronic chips may be located along the lengths of straight-routed conductors.

An implantable medical lead 10 is disclosed herein. The lead 10 may be configured such that tensile loads exerted on the lead body 50 are transferred generally directly to cable conductors 85, polymer tubes 90, or other longitudinally extending structural elements longitudinally extending through the body 50. This transfer of the tensile loads from the lead body 50 to the structural elements 85, 90 may be accomplished by routing the structural elements 85, 90 over and around mechanical termination members 150. Depending on the embodiment, the mechanical termination members 150 may be in the form of a stylet stop 150a, a lead connector termination 150b, or etc. A lead body 50 may include one or more of these types of mechanical termination members 150. A mechanical termination member 150 may be physically constrained within the lead body 50 by layers or other structural aspects of the body 50 such that, for the mechanical termination member 150 to be pulled free from its being constrained, the layers or other structural aspects of the body 50 would undergo being forcibly displaced outwardly.

Depending on the embodiment, a mechanical termination member 150 may have an outer surface that includes gripping features to enhance the engagement between the member 150 and any structural elements 85, 90 coupled thereto. The gripping features may take the form of helical threads, which allow a snug-fitting mechanical termination member 150 to be "screwed" into a subassembly such as, for example, a lead connector end subassembly, thereby facilitating installation. The gripping features may also be straight or helical grooves, which serve to help captivate individual structural elements 85, 90, adding strength and positional control. Electrical isolation of two conductors 85 should be maintained for the two conductors 85 despite being in virtual contact with the mechanical termination members 150. Therefore, the members 150 may be formed from a rigid, but electrically non-conductive material such as, for example, PEEK.

Constraining elements such as, for example, shrink tubing and encapsulating polymers (e.g., reflowed silicone rubber—polyurethane—copolymer ("SPC")) may extend about the structural elements 85, 90 routed over and about the mechanical termination member 150. Employing such constraining elements in such an arrangement may bolster the mechanical strength of the coupling of the structural elements 85, 90 to the member 150.

Figure 2:
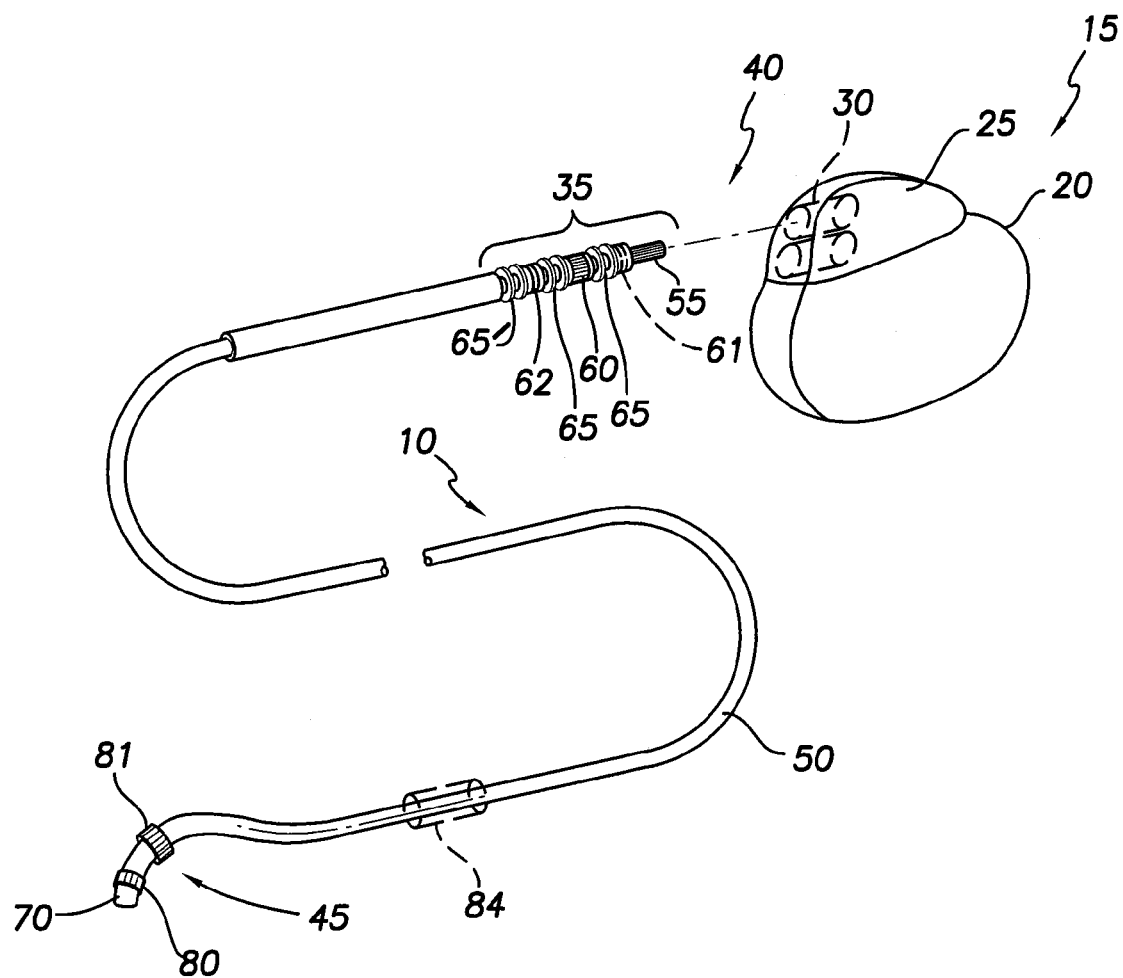
FIG. 2 is an isometric view of an implantable medical lead and a pulse generator for connection thereto.

For a general discussion of embodiments of a lead 10 that may employ the mechanical termination members 150, reference is made to FIGS. 1 and 2, which, are respectively, a side view and an isometric view of implantable medical leads 10 and pulse generators 15 for connection thereto. The pulse generator 15 may be a pacemaker, defibrillator, ICD or neurostimulator. As indicated in FIGS. 1 and 2, the pulse generator 15 may include a can 20, which may house the electrical components of the pulse generator 15, and a header 25. The header may be mounted on the can 20 and may be configured to receive a lead connector end 35 in a lead receiving receptacle 30.

As shown in FIGS. 1 and 2, in one embodiment, the lead 10 may include a proximal end 40, a distal end 45 and a tubular body 50 extending between the proximal and distal ends. In some embodiments, the lead may be a 6 French lead, as manufactured by St. Jude Medical of St. Paul, Minn. In other embodiments, the lead 10 may be larger or smaller than 6 French.

As indicated in FIGS. 1 and 2, the proximal end 40 may include a lead connector end 35 including a pin contact 55, a first ring contact 60, a second ring contact 61, a third ring contact 62, and sets of spaced-apart seals 65. In some embodiments, the lead connector end 35 may include the same or different seals and may include a greater or lesser number of contacts. The lead connector end 35 may be received in a lead receiving receptacle 30 of the pulse generator 15 such that the seals 65 prevent the ingress of bodily fluids into the respective receptacle 30 and the contacts 55, 60, 61 electrically contact corresponding electrical terminals within the respective receptacle 30.

As illustrated in FIGS. 1 and 2, in some embodiments, the body 50 of the lead 10 may be configured for passive fixation. As shown in FIG. 2, the lead distal end 45 may include a distal tip 70, a distal ring electrode 80 and a proximal ring electrode 81. As shown in FIG. 1, the lead body 50 may include a series of electrodes 80, 81, 82, 83 that may be electrodes each equipped with an application-specific integrated circuit ("ASIC") chip. Depending on the embodiment, the lead may have a single conductor, two conductors, three conductors, four conductors, and so forth. Similarly, depending on the embodiment, the lead connector end may be configured for one through four or more conductors.

In some embodiments, the lead 10 may be configured for active fixation. For such a lead, the distal end 45 may include a helical anchor that is extendable from within the distal tip 70 for active fixation. The helical anchor may or may not act as an electrode.

As shown in FIG. 2, in some embodiments, the distal end 45 may include a defibrillation coil 84 about the outer circumference of the lead body 50. The defibrillation coil 84 may be located proximal of the ring electrode 70.

As indicated in FIGS. 1 and 2, the distal electrode 80 may be located near the distal tip 70 of the lead body 50. In some embodiments, the distal electrode 80 may even form the distal tip 70. The rest of the electrodes 81-83 are located proximally from the distal electrode. The electrodes 80-83 may extend about the outer circumference of the lead body 50. Depending on the embodiment, the lead body 50 may include a greater or lesser number of electrodes 80-81 than what is depicted in FIGS. 1 and 2. Also, the electrodes 80-81 may be arranged in similar or different configurations as compared to what is depicted in FIGS. 1 and 2.

Figure 3:
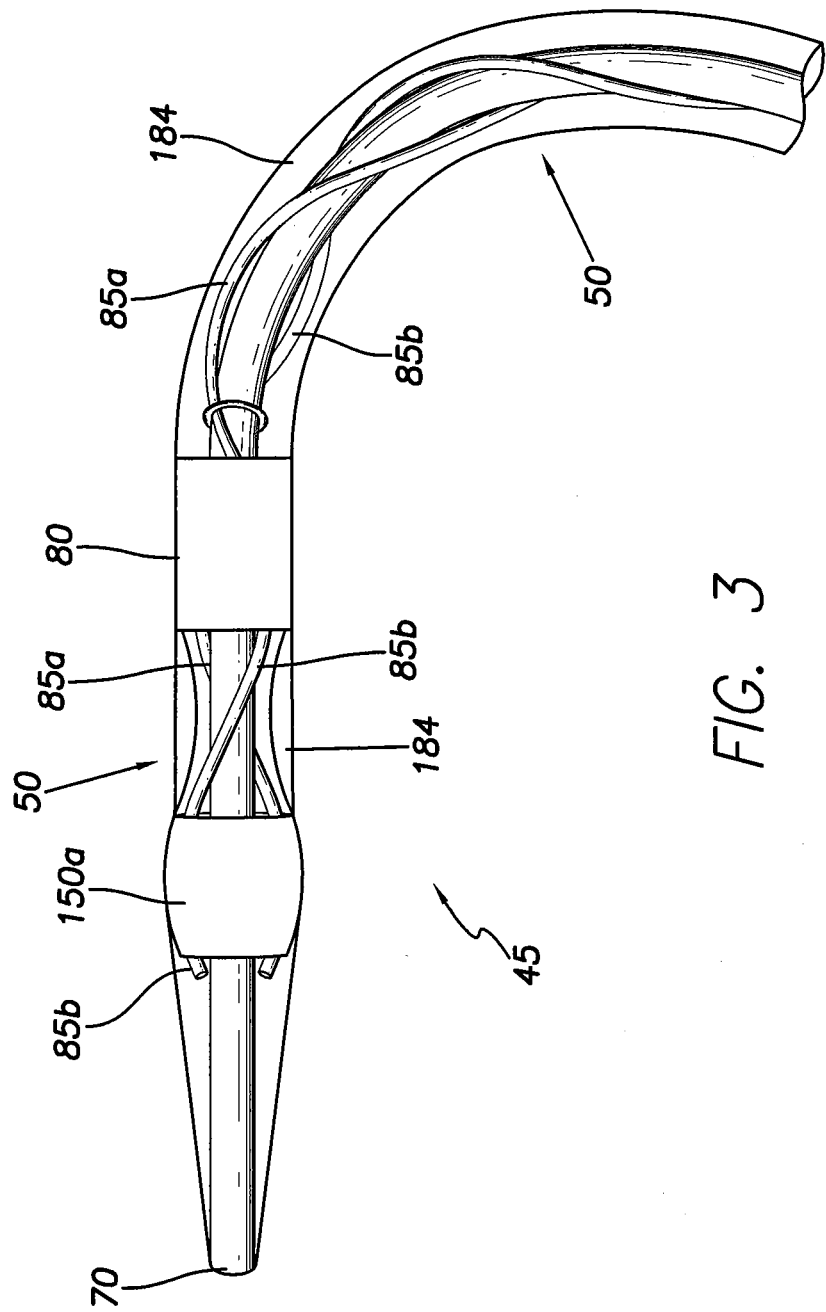
FIG. 3 is an enlarged side view of the distal end of a lead body similar to that described above with respect to FIG. 2.

As can be understood from FIG. 2, in one embodiment, distal electrode 80 may be in electrical communication with the pin contact 55 via a first electrical conductor 85a (see FIG. 3) and the electrode 81 may be in electrical communication with the first ring contact 60 via a second electrical conductor 85b (see FIG. 3). In some embodiments, the defibrillation coil 84 may be in electrical communication with the second ring contact 61 via a third electrical conductor or pair of conductors. In yet other embodiments, other lead components (e.g., additional electrodes, various types of sensors, etc.) mounted on the lead body distal region 45 or other locations on the lead body 50 may be in electrical communication with a third ring contact 62 similar to the second ring contact 61 via a fourth electrical conductor or pair of electrical conductors. Of course, if needed, electrical conductors in addition to the four conductors already mentioned may be routed through the lead body in a manner similar to that already discussed. Depending on the embodiment, any one or more of the conductors may be a multi-strand or filar cable or a single solid wire conductor run singly or grouped.

As can be understood from FIG. 1, in one embodiment, all of the electrodes 80-83 may be in electrical communication with some or all of the contacts 55, 60-62 via first and second electrical conductors 85a, 85b (see FIG. 3) or first, second and third conductors 85a, 85b, 85c (see FIG. 1). Of course, if needed, electrical conductors in addition to the three conductors already mentioned may be routed through the lead body in a manner similar to that already discussed. Depending on the embodiment, any one or more of the conductors may be a multi-strand or filar cable or a single solid wire conductor run singly or grouped.

For a detailed discussion regarding a mechanical termination member 150 employed at a distal end 45 of the lead body 50, reference is made to FIG. 3, which is an enlarged side view of the distal end 45 of a lead body 50 similar to that described above with respect to FIG. 2. As shown in FIG. 3, the lead body 50 may extend proximally from the lead distal tip 70. An electrode 80 may be located proximal of the lead distal tip 70, and the distal mechanical termination member 150a, which may be in the form of a stylet stop 150a, may be located between the distal tip 70 and the electrode 80. As can be understood from FIG. 2, conductors 85a, 85b extend distally through the lead body 50 and electrode 80 to terminate at the stylet stop 150a. More specifically, the conductors 85a, 85b may extend along and about the stylet stop 150a such that the conductors may even distally extend past the distal edge of the stylet stop 150a, as can be seen with respect to conductor 85b in FIG. 3. The conductors 85a, 85b may be traditional straight-routed cable conductors or may be helically routed cable conductors as indicated in FIG. 3 and disclosed in U.S. patent application Ser. No. 12/400,564, filed Mar. 9, 2009, titled "Implantable Medical Lead Having a Body with Helical Cable Conductor Construction and Method of Making Same" and incorporated by reference herein in its entirety. While two conductors 85a, 85b are depicted in FIG. 3, in other embodiments, there may be a greater or lesser number of conductors.

Figure 13:
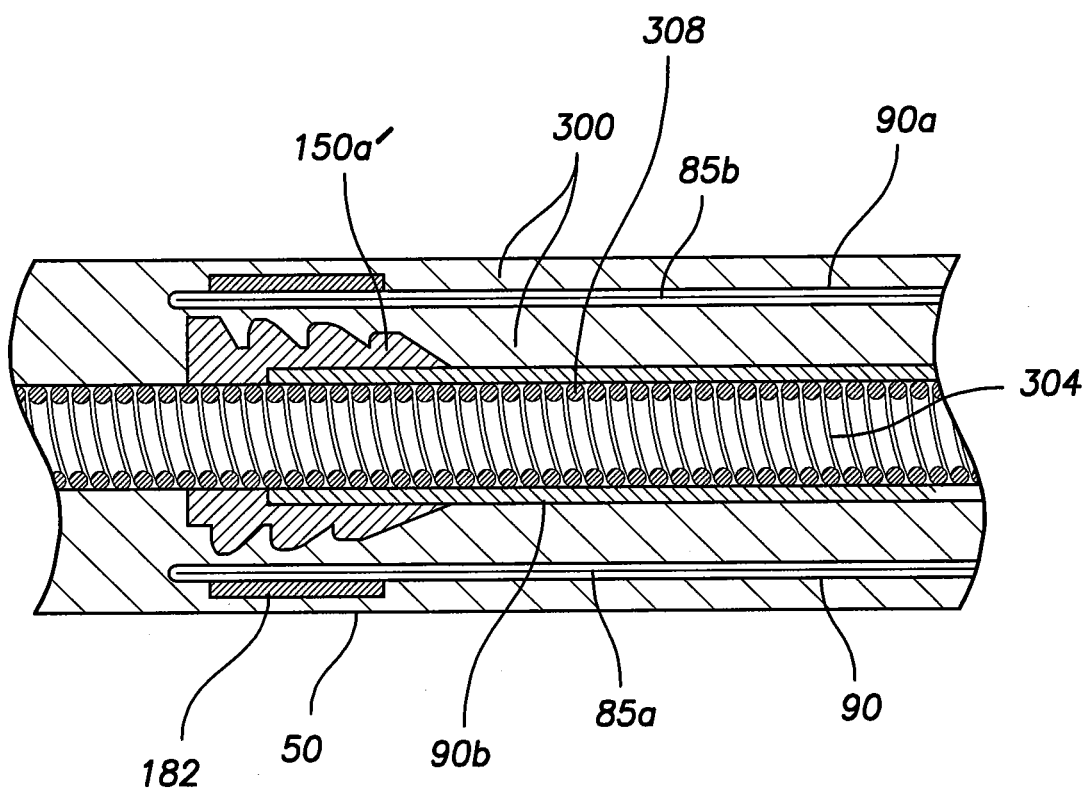
FIG. 13 is a longitudinal cross section of a portion of the lead body including the stylet stop.

As can be understood from FIG. 13, which is a longitudinal cross section of a portion of the lead body 50 including the stylet stop 150a, the conductors 85a, 85b may extend through lumens 90, 90a defined in the wall 300 of the lead body 50. In some embodiments, the wall lumens 90, 90a may be tubular structures 90, 90a that are imbedded in the material of the wall 300 and which may be mechanically connected to the distal and/or proximal mechanical termination members 150. The tubular structures 90, 90a may be formed of polytetrafluoroethylene ("PTFE"), or other polymer materials.

A central lumen 304 may be defined by another tubular structure 90b and may be mechanically connected to the distal and/or proximal mechanical termination members 150. The tubular structure 90b may be formed of polytetrafluoroethylene ("PTFE"), or other polymer materials. The tubular structures 90, 90a, 90b may be mechanically connected to the mechanical termination members 150 such that any tensile force arising in the lead body 50 is transferred to the tubular structures 90, 90a and/or the wall conductors 85 as discussed herein.

In some embodiments, the lead may include a helical inner coil conductor 308 that may form the central lumen 304 and provide power to a distal tip electrode. Depending on the embodiment, the helical inner coil conductor 308 may or may not be mechanically connected to the mechanical termination members 150.

As can be understood from FIGS. 3 and 13, in some embodiments, the conductors 85a, 85b, which may be conductors routed through the wall 300 of the lead body 50, may be mechanically connected to the distal mechanical termination member 150a despite being electrically connected to electrodes 80 that are proximal of the member distal 150a. Thus, the wall conductors 85a, 85b may have structural connections or anchoring points within the body 50 via the mechanical connections between the conductors 85a, 85b and the stylet stop 150a that are separate and distinct from the electrical connections between the conductors 85a, 85b and the electrodes 80. Thus, the tensile loads may encountered by the lead body 50 may be borne by the mechanical connections between the conductors 85a, 85b and the stylet stop 150a as opposed to the electrical connections between the conductors 85a, 85b and the electrodes 80.

As can be understood from FIGS. 1-3 and 13, in one embodiment, the lead 10 includes a tubular body 50 and a structure, such as a conductor 85 and/or tube 90. The tubular body 50 includes a distal end and a proximal end. The body is configured to receive the stylet. The structure 85 and/or 90, 90a longitudinally extends through a wall 300 of the body 50 between the distal end and the proximal end. The structure 85 and/or 90, 90a is anchored within the body 50 such that a tensile force arising within the body 50 by the stylet being extended through the body 50 is substantially carried by the structure 85 and/or 90.

For a discussion regarding the components and assembly of the distal mechanical termination member 150a shown in FIG. 3, reference is made to FIGS. 4A-4E, which are, respectively, distal isometric, side, distal end, proximal end, and longitudinal cross sectional views of a stylet stop shell 150a' of the stylet stop 150a. As shown in FIGS. 4A-4E, the shell 150a' may be generally cylindrical in shape and have an outer surface 160, which may have threads 162 defined therein, The shell 150a' may also include a generally cylindrical opening 164 extending longitudinally through the shell 150a'. The opening 164 may have a stepped inner circumferential surface 166, as indicated in FIG. 4E. The shell 150a' may include a proximal end 168 and a distal end 170, which may have a slot 172 defined therein for receiving a screwdriver type tool during the assembly of the stylet stop 150a into the lead body 50. The shell 150a' may be formed of an electrically insulating material such as, for example, polyetheretherketone ("PEEK") or etc.

Figure 5:
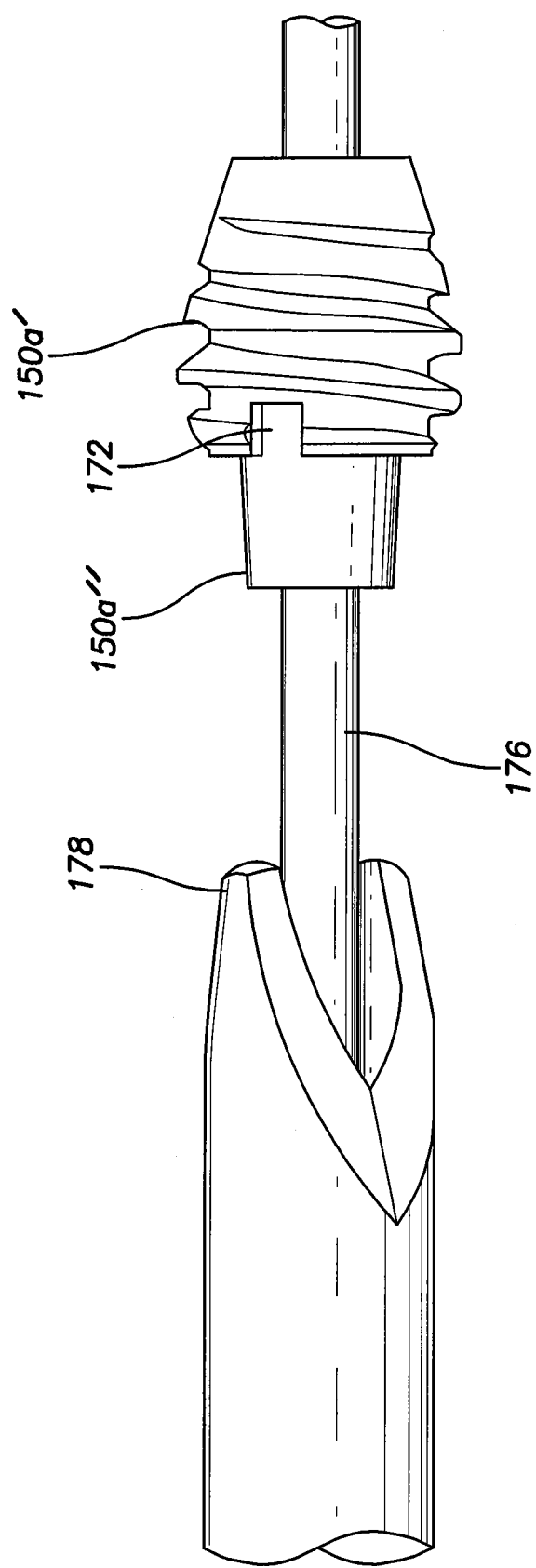
FIG. 5 is a side view of the shell and stop insert being assembled on an assembly guide mandrel.

In some embodiments, the shell 150a' may include a separate stop insert 150a" and together form the stylet stop 150a. As indicated in FIG. 5, which is a side view of the shell 150a' and stop insert 150a" being assembled on an assembly guide mandrel 176, the stop insert 150a" may be received in the shell 150a' to occupy the shell opening 164 shown in FIGS. 4C-4E. The stop insert 150a" may be formed of a material such as, for example, stainless steel, or etc. A screwdriver type tool 178 may engage the slot 172 to cause the stylet stop 150a to be threaded via the stop's threads 162 into the distal end of an inner layer or tubing 180 of the lead body 50, as can be understood from FIG. 6, which is a side view of the stylet stop 150a assembled on the assembly mandrel 176 and received within the distal end of the inner layer or tubing 180 of the lead body 50. The inner layer or tubing 180 of the lead body 50 may include the conductors 85a, 85b and may also be on the mandrel 176.

Figure 6:
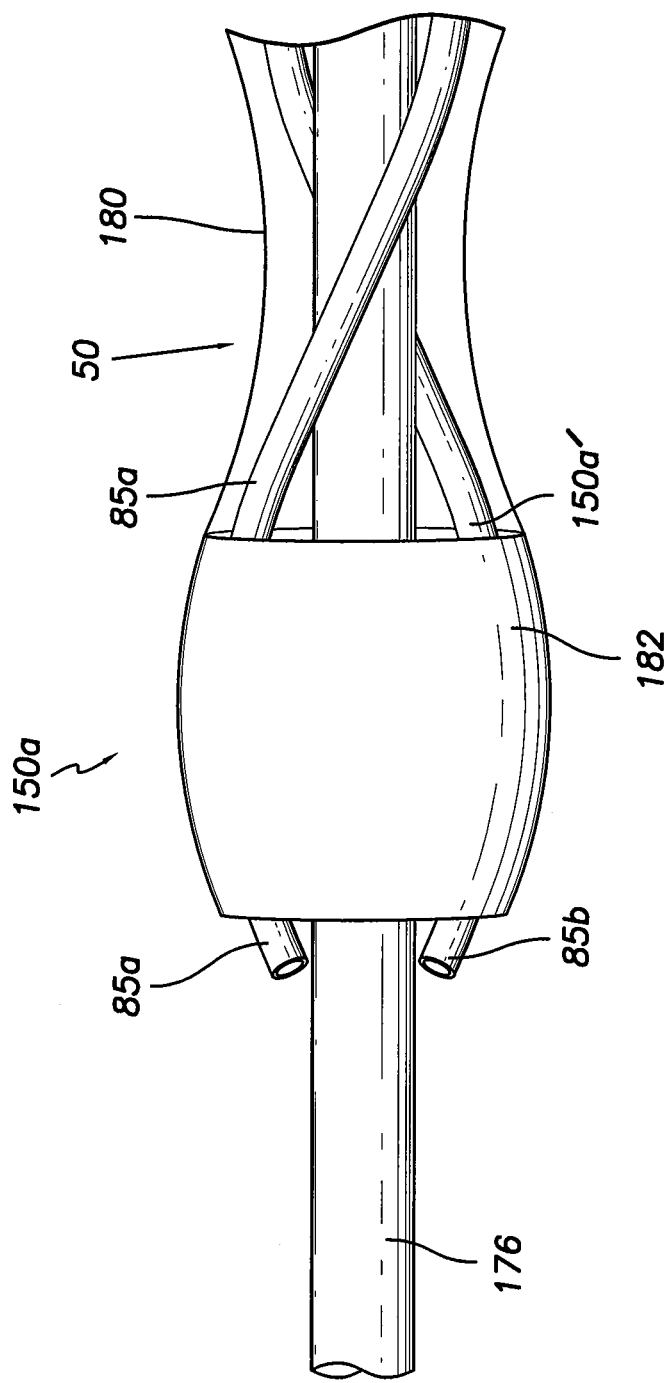
FIG. 6 is a side view of the stylet stop assembled on the assembly mandrel and received within the distal end of the inner layer or tubing of the lead body.

As shown in FIG. 6, a binding element 182 in the form of a metal or polymer band, snap rings, or a heat shrink tube segment may used to further secure the stylet stop 150a within the inner layer or tubing 180. For example, in the context the binding element 182 being a segment of heat shrink tube 182, the heat shrink tube segment 182 may be located and heat shrunk about the tubing 180 in the region occupied by the stylet stop 150 to further secure the stylet stop 150 within the inner layer or tubing 180 of the lead body 50. The extreme distal ends of the conductors 85a, 85b may extend distally past the distal edges of the stylet stop 150 and the heat shrink tube 182. The proximal edge of the stylet stop 150 may extend proximally past the proximal edge of the heat shrink tube 182. The heat shrink tube 182 may be formed of fluorinated ethylene propylene ("FEP"), etc., and the inner layer or tube 180 may be formed of silicone rubber, polyurethane, SPC, etc.

In one embodiment, when the subassembly at the distal end of the lead body 50 is completed as discussed with respect to FIG. 6, the subassembly is ready for the outer insulation layer 184 (see FIG. 3) of the lead body 50 to be deposited about the inner layer 180 and shrink tube 182 to form the completed lead body 50 depicted in FIG. 3. The outer insulation layer 184 may be deposited about the outer surfaces of the inner layer 180 and shrink tube 182 via various methods, including, reflow, coextrusion, etc. The outer insulation layer 184 may be formed of silicone rubber, polyurethane, silicone rubber—polyurethane—copolymer ("SPC"), etc.

While, in some embodiments, the stylet stop 150 may be located distal of a most distal electrode, in some embodiments, the stylet stop 150 may be located proximal of a most distal electrode. In some embodiments, there may be electrodes located distal and proximal of the stylet stop 150.

In some embodiments, the stylet stop 150 may be configured to have a fluted design with helical grooves that are similar to the helical grooves 210 of the fluted design employed with the proximal mechanical termination member 150 discussed with respect to FIGS. 11 and 12 discussed below.

Figure 7:
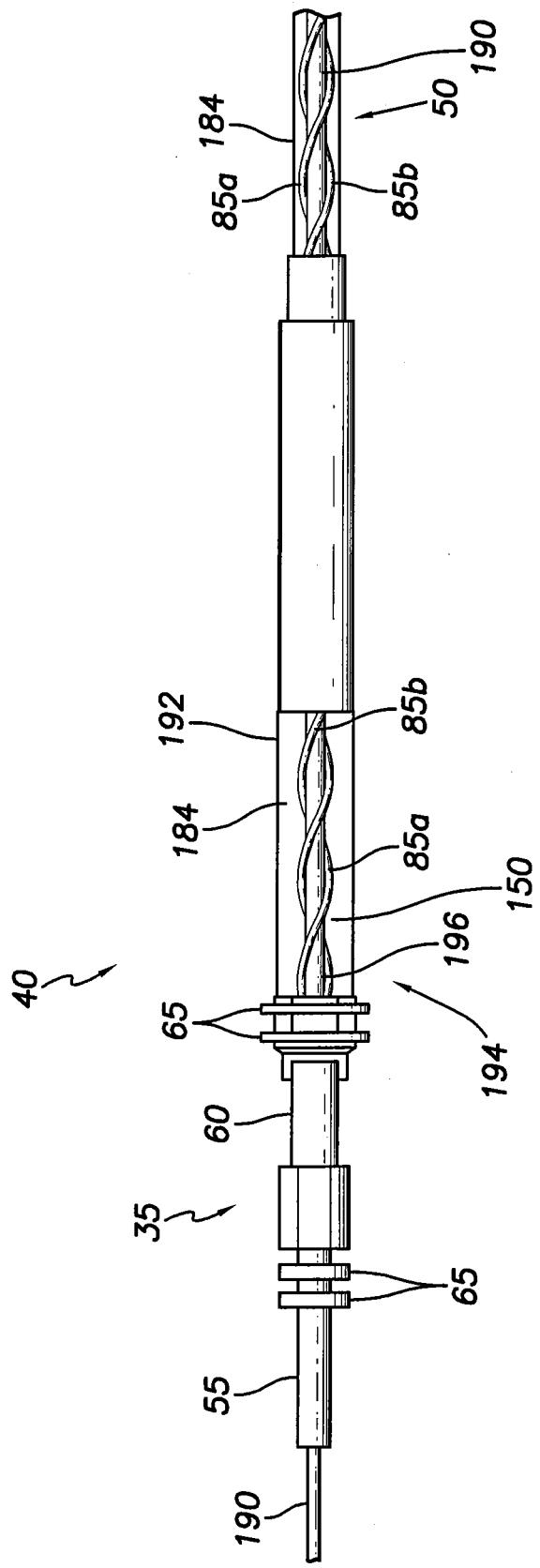
FIG. 7 is an enlarged side view of the proximal end of a lead body similar to that described above with respect to FIG. 2.
Figure 8:
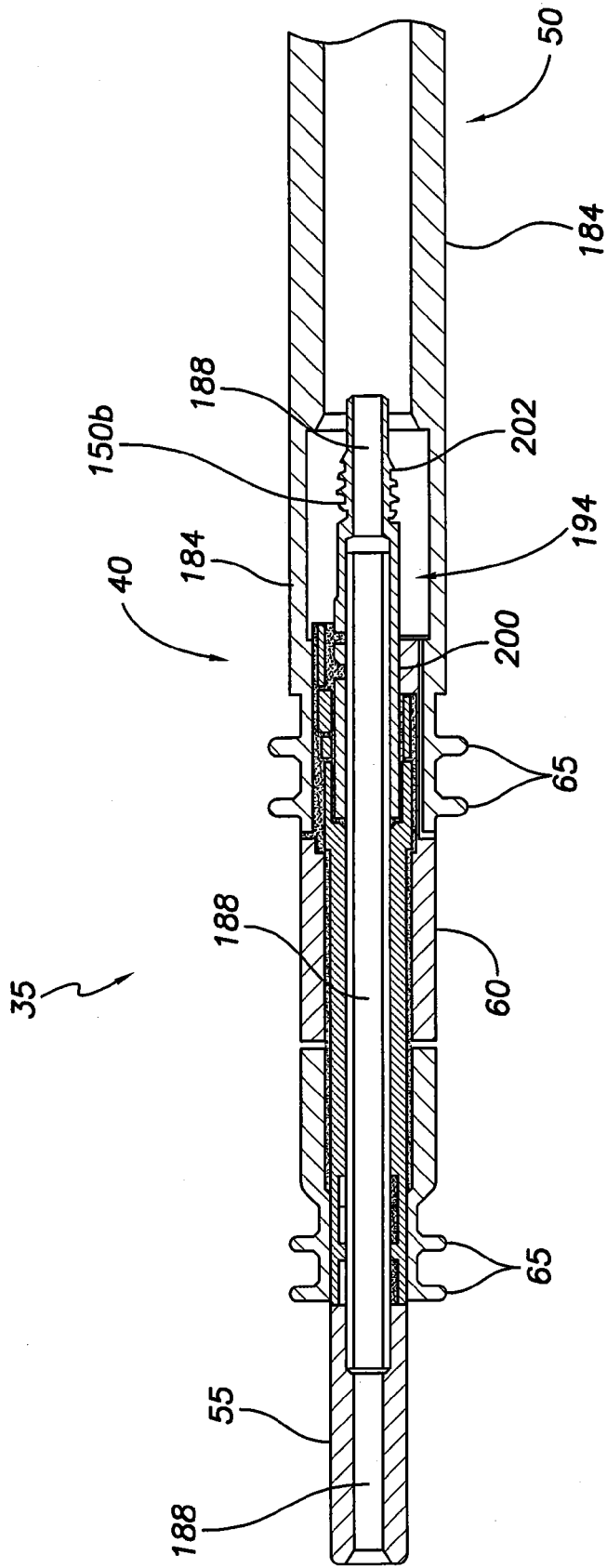
FIG. 8 is a longitudinal cross section of the proximal end of the lead body depicted in FIG. 7.

For a detailed discussion regarding a mechanical termination member 150 employed at a proximal end 40 of the lead body 50, reference is made to FIGS. 7 and 8. FIG. 7 is an enlarged side view of the proximal end 40 of a lead body 50 similar to that described above with respect to FIG. 2. FIG. 8 is a longitudinal cross section of the proximal end 40 of the lead body depicted in FIG. 7.

As shown in FIGS. 7 and 8, the lead body 50 may extend distally from the lead connector end 35 that includes the ring contact 60, the seals 65, and the pin contact 55, which forms the proximal extremity of the lead 10. As can be understood from FIGS. 7 and 8, a central lumen 188 may extend through the pin contact 55, the lead connector end 35 and the lead body 50 and may be configured to allow a member 190 to be extended through the central lumen 188. In the context of the lead 10 being assembled during the manufacturing process, the member 190 may be an assembly mandrel 190. In the context of the lead 10 being delivered to the implantation site during a lead implantation procedure, the member 190 may be a guidewire or stylet 190.

As shown in FIG. 7, a suture sleeve or flex reinforcing sleeve 192 may extend over the junction between the proximal end of the lead body 50 and the distal end of the lead connector end 35. As depicted in FIGS. 7 and 8, the proximal mechanical termination member 150b may be in the form of a distal tail end 150b of the subassembly 194 of the lead connector end 35. The outer insulation layer 184 of the lead body 50 at the proximal end of the lead body 50 may extend about the proximal termination member 150b, and the sleeve 192 may extend about the outer insulation layer 184

Figure 9:
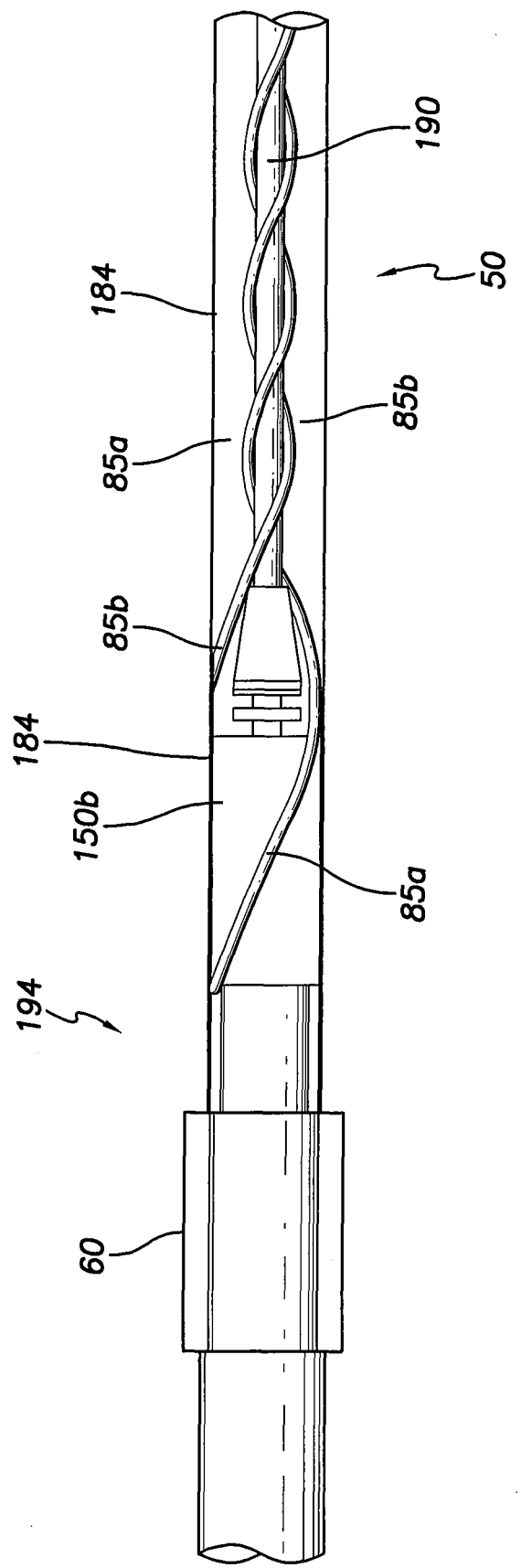
FIG. 9 is an enlarged view of the subassembly of the lead connector end of FIG. 7.

As can be understood from FIG. 7, conductors 85a, 85b extend proximally through the lead body 50 and over the proximal termination member 150b. As indicated in FIG. 7 and FIG. 9, which is an enlarged view of the subassembly 194 of the lead connector end 35 of FIG. 7, in some embodiments, the conductors 85a, 85b extend into the lead connector end 35 via openings 196 in the proximal termination member 150b and/or via the distal end opening of the distal extension of the ring contact 60. As mentioned above, the conductors 85a, 85b may be traditional straight-routed cable conductors or may be helically routed cable conductors as indicated in FIGS. 7 and 9 and disclosed in U.S. patent application Ser. No. 12/400, 564, filed Mar. 9, 2009, titled "Implantable Medical Lead Having a Body with Helical Cable Conductor Construction and Method of Making Same" and incorporated by reference herein in its entirety. While two conductors 85a, 85b are depicted in FIGS. 7 and 9, in other embodiments, there may be a greater or lesser number of conductors.

Figure 10A:
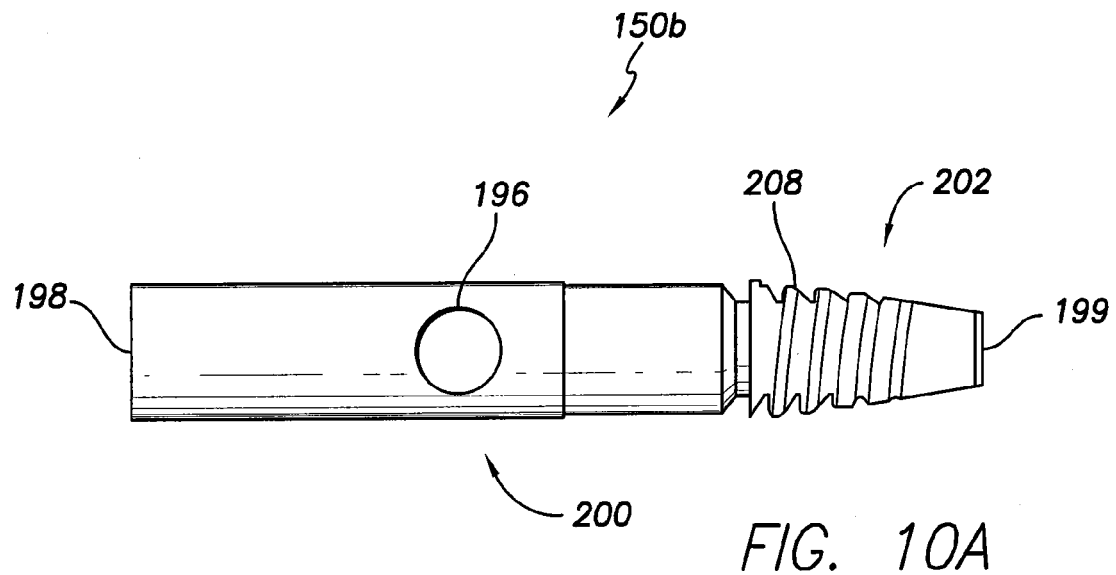
FIGS. 10A and 10B are, respectively, a longitudinal side view and a longitudinal cross section of a proximal termination member of the lead connector end of FIG. 7.
Figure 10B:
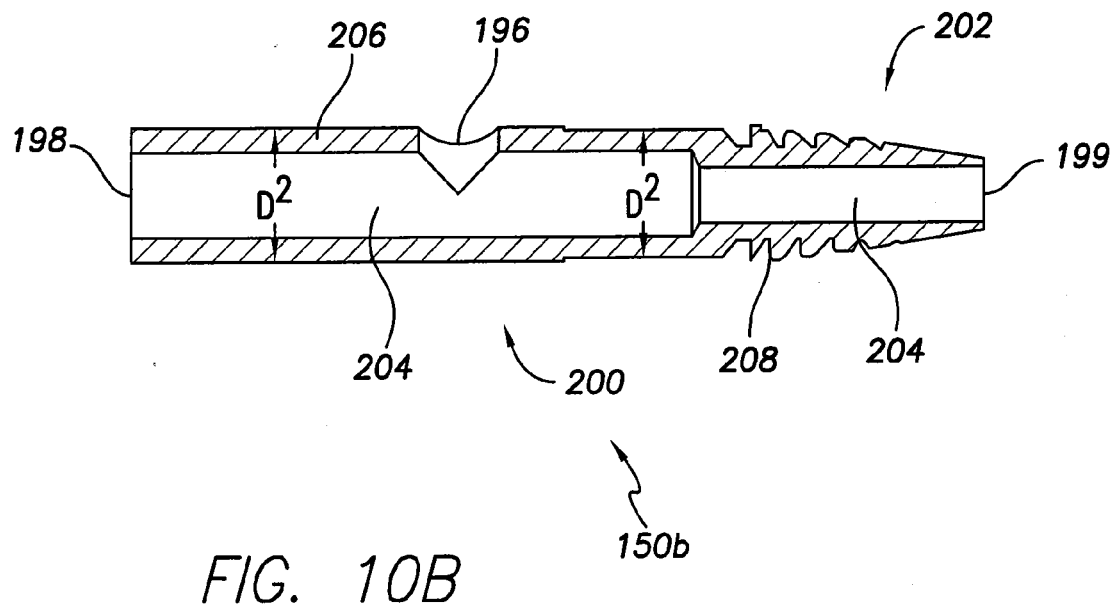

For a discussion regarding the components and assembly of the proximal mechanical termination member 150b shown in FIGS. 7-9, reference is first made to FIGS. 10A-10B, which are, respectively, a longitudinal side view and a longitudinal cross section of a first embodiment of the proximal termination member 150b. As shown in FIGS. 10A-10B, the first embodiment of the proximal member 150b may include a proximal end 198, a distal end 199, a proximal cylindrical portion 200, a distal tapered portion 202, and a central lumen 204 extending longitudinally through the member 150b. The proximal cylindrical portion 200 may have a stepped configuration having a proximal diameter D1 that is greater than a distal diameter D2. The proximal cylindrical portion 200 may also include one or more openings 196 extending through the wall 206 of the member 150b to open into the lumen 204. As mentioned above, one or more conductors 85 may extend through the one or more openings 196. The central lumen 204 may form part of the central lumen 188 of the overall lead connector end 35 and lead body 50 (see FIG. 8). The tapered portion 202 may include threads 208 extending along the exterior of the tapered portion 202.

As indicated in FIG. 11, which is a longitudinal side view of a second embodiment of the proximal termination member 150b, the proximal member 150b may include a proximal end 198, a distal end 199, a proximal cylindrical portion 200, an intermediate necked-down portion 201, a distal tapered portion 202, and a central lumen 204 extending longitudinally through the member 150b. The proximal cylindrical portion 200 may have a diameter D1 substantially greater than the diameter D2 of the intermediate necked-down portion 201. The proximal cylindrical portion 200 may also include one or more openings in a distal face 205 of the proximal cylindrical portion 200 or one or more openings in the sidewall of the proximal cylindrical portion 200 similar to that depicted in FIGS. 10A-10B. The one or more openings may open into the lumen 204. As mentioned above, one or more conductors 85 may extend through the one or more openings 196. The central lumen 204 may form part of the central lumen 188 of the overall lead connector end 35 and lead body 50 (see FIG. 8). The tapered portion 202 may include flutes 210 extending along the exterior of the tapered portion 202. Regardless of whether the first embodiment (FIGS. 10A-10B) or the second embodiment (FIG. 11) is employed, the proximal member 150b may be formed of an electrically insulating material such as, for example, polyetheretherketone ("PEEK"), or etc.

As can be understood from FIGS. 7-9, for both embodiments of the proximal mechanical termination member 150b, the proximal cylindrical portion 200 of the member 150b may be received within and secured to a distal portion of the ring contact 60 or another structural aspect of the lead connector end 35. The conductors 85a, 85b may extend over the distal tapered portion 202.

As can be understood from FIGS. 7 and 9, for the first embodiment of the member 150b, the conductors 85a, 85b may be routed over the threads 208 in a helical or straight fashion, depending on routing used throughout the rest of the lead body 50. As can be understood from FIG. 12, which is the same view as FIG. 11, except with the conductors extending along the proximal portion 202, the conductors 85a, 85b are routed along the flutes 210, which may extend helically or straight along the proximal portion 202.

In either case, as best understood from FIG. 12, but is also the case in FIGS. 7 and 9, in one embodiment, the inner layer or tubing 180 of the lead body 50 extends over the conductors 85a, 85b and proximal portion 202 of the proximal termination member 150b to cause the conductors 85a, 85b to be gripped against the threads (FIGS. 7 and 9) or within the flutes 210 (FIG. 12). The conductors 85a, 85b may be further mechanically secured to the proximal portion 202 of the proximal termination member 150b via the outer insulation layer 184 (see FIGS. 7 and 9), which extends over the inner tubing 180. Yet further securing of conductors 85a, 85b to the proximal portion 202 of the proximal termination member 150b may be provided via the presence of the sheath 192 discussed above with respect to FIG. 7. As with the assembly of the distal member 150a discussed above with respect to FIGS. 5-6, a mandrel extended through the central lumen 188 may also be employed in the assembly of the proximal member 150b.

In a manner similar to that discussed above with respect to FIG. 6, in some embodiments, a binding element in the form of a metal or polymer band, snap rings, or a heat shrink tube segment may used to further secure the proximal member 150b within the inner layer or tubing 180. For example, in the context the binding element being a segment of heat shrink tube, the heat shrink tube segment may be located and heat shrunk about the tubing 180 in the region occupied by the proximal portion 202 of the proximal member 150b to further secure the proximal member 150b within the inner layer or tubing 180 of the lead body 50. The extreme proximal ends of the conductors 85a, 85b may extend proximally past the proximal edges of the proximal member 150b and the heat shrink tube to be electrically coupled to the respective contacts 55, 60 of the lead connector end 35. The heat shrink tube and inner layer may be formed of the same material as discussed above with respect to the distal member 150a.

In one embodiment, when the subassembly 194 at the proximal end of the lead body 50 is completed as discussed with respect to FIGS. 8 and 12, the subassembly is ready for the outer insulation layer 184 (see FIGS. 7 and 9) of the lead body 50 to be deposited about the inner layer 180 and shrink tube to form the completed lead body 50 depicted in FIG. 7. The outer insulation layer 184 may be deposited about the outer surfaces of the inner layer 180 and shrink tube via various methods, including, reflow, coextrusion, etc. The outer insulation layer 184 may be formed of silicone rubber, polyurethane, SPC, etc.

In general, most, if not all, features of the proximal and distal members 150 may be employed with either type of member 150. For example, any of the binding elements may apply to either of the proximal and distal members 150 regardless of the type or location on the lead. Also, the proximal member 150b may be located on the lead body at locations other than the proximal portion of the lead. Similarly, the distal member 150a may be located on the lead body at locations other than the distal portion of the lead.

Although the present invention has been described with reference to preferred embodiments, persons skilled in the art will recognize that changes may be made in form and detail without departing from the spirit and scope of the invention.

What is claimed is:

1. A method of assembling an implantable medical lead, the method comprising:
   providing a tubular insulation layer;
   disposing an electrode on the tubular insulation layer;
   routing an electrical conductor through the tubular insulation layer;
   inserting a stylet stop into a distal end of the tubular insulation layer, wherein the electrical conductor is positioned between the tubular insulation layer and the stylet stop, and wherein the electrical conductor is directly and mechanically connected to the stylet stop and in electrical communication with the electrode; and
   applying a heat shrink layer around a portion of the tubular insulation layer extending around the stylet stop.

2. The method of claim 1, further comprising threading the stylet stop into the tubular insulation layer.

3. The method of claim 1, further comprising providing a grooved member in a proximal end of the tubular insulation layer and routing the conductor along a groove extending along the grooved member.

4. The method of claim 3, further comprising helically routing the groove along the grooved member.

5. The method of claim 3, further comprising cylindrically shaping or distally tapering the groove along the grooved member.

6. The method of claim 1, further comprising providing the electrical conductor with an electrically conductive core and an electrical insulation jacket.

7. The method of claim 1, wherein the electrode is a most distal electrode and the stylet stop is distal of the electrode.

8. A method of assembling an implantable medical lead, the method comprising:
   providing a tubular insulation layer;
   disposing an electrode on the tubular insulation layer;
   routing an electrical conductor through the tubular insulation layer;
   inserting a stylet stop into a distal end of the tubular insulation layer, wherein the electrical conductor is positioned between the tubular insulation layer and the stylet stop, and wherein the electrical conductor is directly and mechanically connected to the stylet stop and in electrical communication with the electrode; and
   providing the stylet stop with and outer shell and directly and mechanically connecting the electrical conductor to the outer shell via a heat shrink layer.

9. The method of claim 8, further comprising providing the stylet stop with an insert portion received in the outer shell and configuring the insert portion to engage a distal end of a stylet.

* * * * *